US00PP09083P

United States Patent [19]

VandenBerg

[11] Patent Number: Plant 9,083

[45] Date of Patent: Mar. 21, 1995

[54] CHRYSANTHEMUM PLANT NAMED TIJUANA

[75] Inventor: Cornelis P. VandenBerg, Salinas, Calif.

[73] Assignee: Yoder Brothers, Inc., Barberton, Ohio

[21] Appl. No.: 280,523

[22] Filed: Jul. 26, 1994

[51] Int. Cl.[6] ..... A01H 5/00

[52] U.S. Cl. ..... Plt./74.1

[58] Field of Search ..... Plt. 74.1

*Primary Examiner*—Howard J. Locker

*Attorney, Agent, or Firm*—Foley & Lardner

[57] ABSTRACT

A Chrysanthemum plant named Tijuana particularly characterized by its flat capitulum form; daisy capitulum type; red-purple and white bi-colored ray floret color; diameter across face of capitulum of 79 to 83 mm when fully opened, when grown as a pinched spray pot mum; photoperiodic flowering response to short days of 51 to 54 days; plant height, with 14 to 15 long days after sticking unrooted cuttings, and with 1 to 2 applications of 2500 ppm B-9 SP, ranges from 25 to 30 cm when grown as a pinched pot mum with four cuttings in a 15 cm pot; branching pattern is spreading and prolific, each plant having 4 to 5 laterals after pinch; and recommended as spray pot mum.

3 Drawing Sheets

The present invention comprises a new and distinct cultivar of Chrysanthemum, botanically known as *Dendranthema grandiflora,* and referred to by the cultivar name Tijuana.

Tijuana, identified as 5289 (91-507001), was originated from a cross made by Cornelis P. VandenBerg in a controlled breeding program in Salinas, Calif., in 1990.

The female parent of Tijuana was an unnamed seedling identified as 6685 (86-881002) and described as a spray pot mum with flat capitulum form; daisy capitulum form; pink and white bi-colored ray floret color; diameter across face of capitulum of 67 to 79 mm when grown as a spray pot mum; flowering response to short days in Salinas, Calif. of 51 to 57 days; plant height of 20 to 28 cm when grown with 15 to 16 long days after sticking unrooted cuttings prior to start of short days and 1 to 2 applications of 2500 ppm B-9 SP; and a branching pattern of 4 to 5 laterals developing after pinch.

The male parent of Tijuana was the cultivar identified as 0458 (87-840003), and described as a cut spray mum with flat capitulum form; daisy capitulum type; pink and white bi-colored ray floret color; diameter across face of capitulum of 79 to 89 mm when grown as a single stem spray cut mum; flowering response to short days in Honselersdijk, The Netherlands of 51 to 56 days; and a plant height of 89 to 114 cm when grown as a single stem cut spray mum with 17 to 21 long days after planting rooted cuttings in Honselersdijk, The Netherlands.

Tijuana was discovered and selected as one flowering plant within the progeny of the stated cross by Cornelis P. VandenBerg in March 1992, in a controlled environment in Salinas, Calif.

The first act of asexual reproduction of Tijuana was accomplished when vegetative cuttings were taken from the initial selection in May 1992 in a controlled environment in Salinas, Calif., by technicians working under supervision of Cornelis P. VandenBerg.

Horticultural examination of controlled flowerings of successive plantings has shown that the unique combination of characteristics as herein disclosed for Tijuana are firmly fixed and are retained through successive generations of asexual reproduction.

Tijuana has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Tijuana, which, in combination, distinguish this Chrysanthemum as a new and distinct cultivar:

1. Flat capitulum form.
2. Daisy capitulum type.
3. Red-purple and white bi-colored ray floret color.
4. Diameter across face of capitulum of 79 to 83 mm when fully opened, when grown as a pinched spray pot mum.
5. Photoperiodic flowering response to short days of 51 to 54 days.
6. Plant height, with 15 to 15 long days after sticking unrooted cuttings, and with 1 to 2 applications of 2500 ppm B-9 SP, ranges from 25 to 30 cm when grown as a pinched pot mum with four cuttings in a 15 cm pot.
7. Branching pattern is spreading and prolific, each plant having 4 to 5 laterals after pinch.
8. Recommended as spray pot mum.

The accomanying photograhic drawings show typical inflorescence and leaf characteristics of Tijuana, with the colors being as nearly true as possible with illustrations of this type.

Sheet 1 is a color photograph of Tijuana grown as a pinched spray pot mum with four cuttings in a 15 cm pot.

Sheet 2 is a black and white photograph of three views of the inflorescence of Tijuana.

Sheet 3 is a black and white photograph showing the upper and under sides of the leaves of Tijuana at three stages of development (mature, intermediate and immature).

In sheets 2 and 3 a measuring tape in centimeters has been added.

Of the commercial cultivars known to the inventor, the most similar in comparison to Tijuana is the cultivar Regal Davis, disclosed in U.S. Plant Pat. No. 8,292. Reference is made to attached Chart A, which compares certain characteristics of Tijuana to the same characteristics of Regal Davis.

Similar traits are capitulum form and type, and recommendation as a pot spray mum. The ray floret color of both Tijuana and Regal Davis is red-purple. However, Tijuana has a red-purple and white bi-color ray floret color, while the ray floret color of Regal Davis is solid red-purple. Tijuana also has a larger diameter of capitulum, an earlier flowering response to short days, a taller plant height, and in some trials one less lateral developing after pinching when compared with Regal Davis.

In the following description color references are made to The Royal Horticultural Society Colour Chart. The color values were determined on plant material grown as a pinched spary pot mum in Salinas, Calif. on Apr. 29, 1994.

Classification:

*Botanical.*—*Dendranthema grandiflora* cv Tijuana.

*Commercial.*—Daisy spray pot mum.

INFLORESCENCE

A. Capitulum:

*Form.*—Flat.

*Type.*—Daisy.

*Diameter across face.*—79 to 83 mm when fully opened.

B. Corolla of ray florets:

*Color (general tonality from a distance of three meters).*—Red-purple and white bi-color.

*Color (upper surface).*—71B with wite bands radiating from the disc.

*Color (under surface).*—70B, streaked with white.

*Shape.*—See photograph.

C. Corolla of disc florets:

*Color (mature).*—14B.

*Color (immature).*—144B.

D. Reproductive organs:

*Androecium..*—Present on disc florets only; moderate pollen.

*Gynoecium.*—Present on both ray and disc florets.

PLANT

A. General appearance:

Height.—25 to 30 cm when grown as a pinched pot mum with four cuttings in a 15 cm pot, and with 14 to 15 long days after direct sticking unrooted cuttings prior to start of short days and 1 to 2 applications of 2500 ppm B-9 SP.

*Branching pattern.*—Spreading and prolific, with 4 to 5 laterals after pinch.

B. Foliage:

*Color (upper surface).*—147A.

*Color (under surface).*—147B.

*Shape.*—See photograph.

CHART A

COMPARISON OF TIJUANA AND REGAL DAVIS

| CULTIVAR | TIJUANA | REGAL DAVIS |
|---|---|---|
| Ray floret color | Red-purple and white bi-color | Solid red-purple |
| Capitulum form and type | Flat daisy | Flat daisy |
| Diameter across face of capitulum | 79 to 83 mm | 64 to 70 mm |
| Flowering response | 51 to 54 days | 55 to 60 days |
| Plant height with 14 to 16 long days | 25 to 30 cm | 20 to 25 cm |
| Branching pattern | 4 to 5 laterals | 4 to 6 laterals |
| Recommended as | Pot spray mum | Pot spray mum |

COMPARISONS MADE OF PLANTS GROWN AS PINCHED SPRAY POT MUMS IN SALINAS, CALIFORNIA

I claim:

1. A new and distinct Chrysanthemum plant named Tijuana, as described and illustrated.

* * * * *

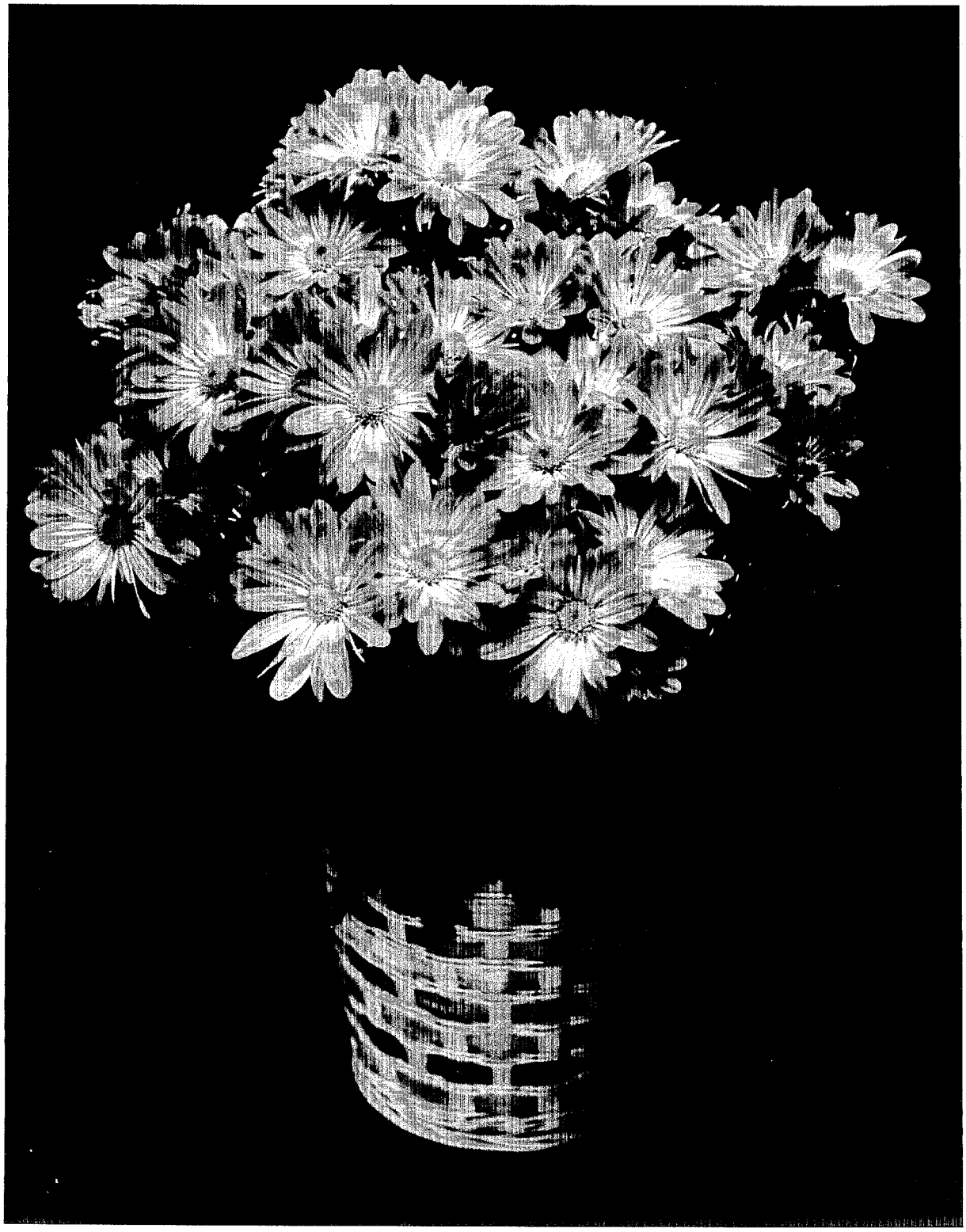

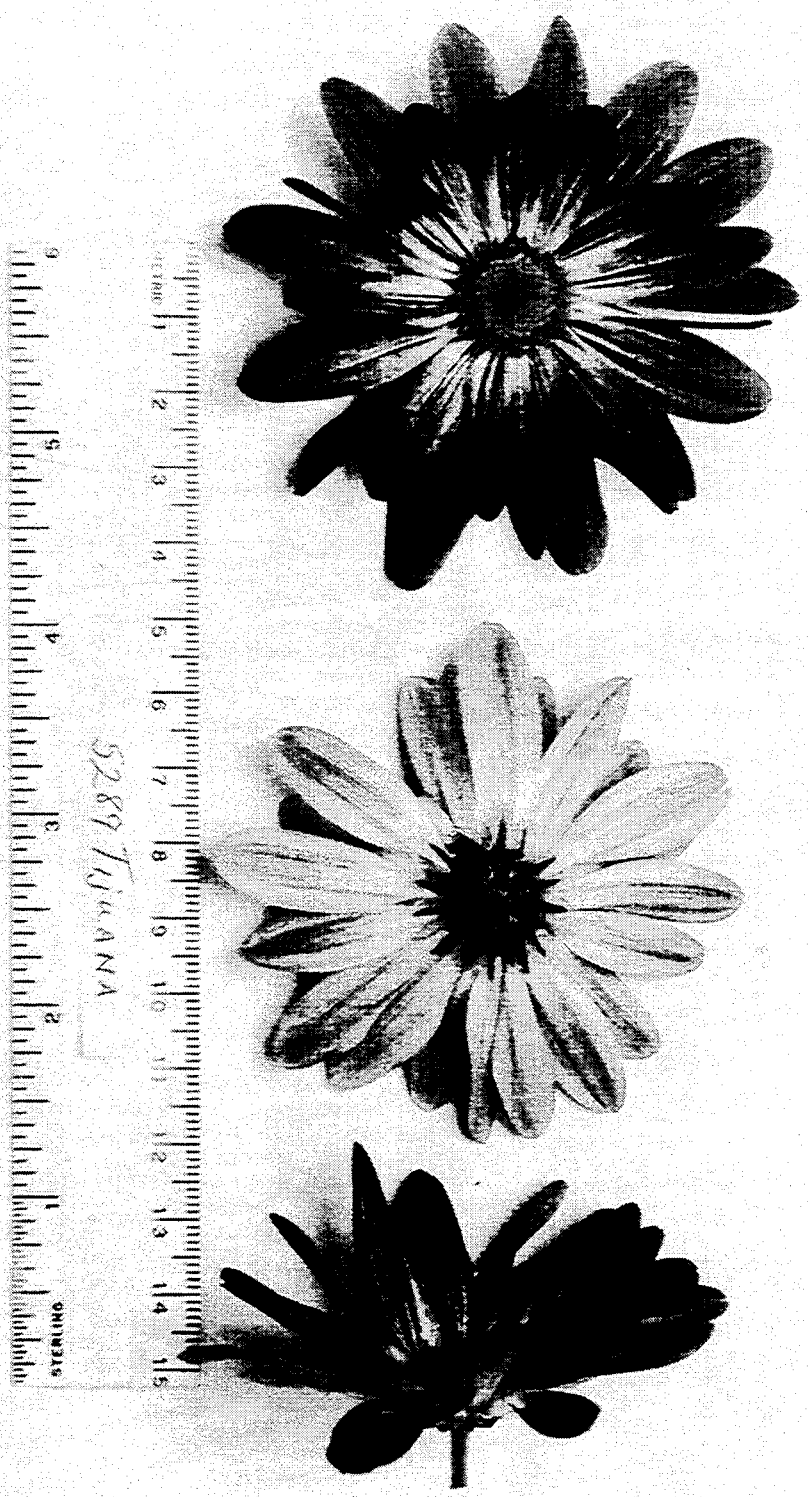
5289 TUSCANA
STERLING

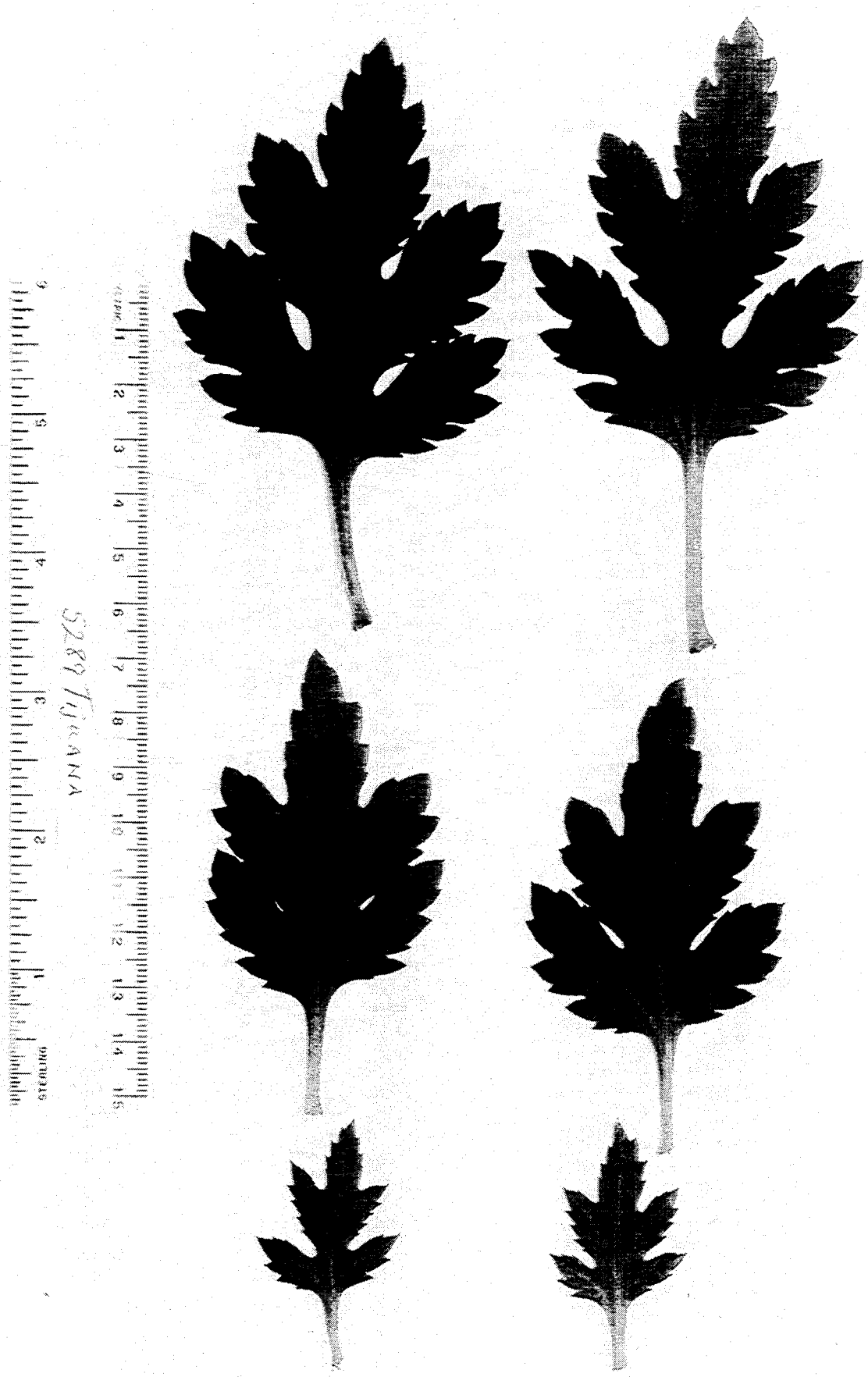
5289 Tijuana